United States Patent
Mastorides et al.

(10) Patent No.: US 6,780,636 B2
(45) Date of Patent: Aug. 24, 2004

(54) CRYOARRAY SYSTEM AND USES THEREOF

(75) Inventors: Stephen Mastorides, Tampa, FL (US); Carlos Cordon-Cardo, New York, NY (US)

(73) Assignee: Sloan Kettering Institute for Cancer Research, New York, NY (US)

(*) Notice: Subject to any disclaimer, the term of this patent is extended or adjusted under 35 U.S.C. 154(b) by 77 days.

(21) Appl. No.: 10/006,775

(22) Filed: Dec. 10, 2001

(65) Prior Publication Data

US 2002/0137198 A1 Sep. 26, 2002

(51) Int. Cl.$^7$ .............................. A01N 1/00; C12M 1/00; C12M 1/34
(52) U.S. Cl. ...................... 435/284.1; 435/6; 435/91.2; 435/283.1; 435/287.2; 435/287.3; 536/23.1; 536/24.3; 536/24.33
(58) Field of Search .......................... 435/283.1, 284.1, 435/287.2, 287.3, 6, 91.2, 286.3, 91.1, 286.2; 536/23.1, 24.3, 24.33; 422/63

(56) References Cited

U.S. PATENT DOCUMENTS

| | | | |
|---|---|---|---|
| 4,654,989 A | * | 4/1987 | Fleming ..................... 40/427 |
| 6,103,518 A | * | 8/2000 | Leighton .................. 435/286.3 |
| 6,298,587 B1 | * | 10/2001 | Vollom ......................... 40/427 |
| 6,534,307 B1 | * | 3/2003 | Muraca .................... 435/286.2 |

OTHER PUBLICATIONS

Hoos et al. (Laboratory Investigation (Oct. 2001) 81(10: 1331–1338).*

Kononen et al. Nature Medicine (1998) 4(7) : 844–847.*

Bubendorf et al. Cancer Research (1999) 59 : 803–806.*

\* cited by examiner

*Primary Examiner*—Carla J. Myers
*Assistant Examiner*—Alexander H. Spiegler
(74) *Attorney, Agent, or Firm*—Benjamin Aaron Adler

(57) ABSTRACT

The present invention provides a method for creating a cryoarray of frozen tissue cores using a cryoarray system. Such system comprises a tissue mold, an embedding medium and a cryoarray device. The cryoarray device comprises a mold plate, an ejector plate, mold alignment pins, ejector pins, and cryoarray pins. Such method/system may be used for preparing frozen sections with multiple tissue specimens for assays such as in-situ hybridization and immunohistochemistry.

11 Claims, 7 Drawing Sheets

CRYOARRAY SYSTEM AND USES THEREOF

BACKGROUND OF THE INVENTION

1. Field of the Invention

The present invention relates generally to the field of molecular pathology and biomedical devices. More specifically, the present invention relates to a cryoarray device/system for creating frozen tissue arrays for subsequent assaying.

2. Description of the Related Art

The implementation of high-throughput genetic technologies, such as oligonucleotide microarrays, generates myriad points of data. The identified potential candidate genes need to be further characterized and selected using a large number of well-characterized tumors and stringent criteria. Tissue microarrays allow for such high-throughput expression profiling of tumor samples, additionally providing information at the microanatomical level.

Sections cut from tissue arrays allow parallel detection of DNA, e.g., by fluorescence in-situ hybridization (FISH), RNA, e.g., by mRNA in-situ hybridization (mRNA ISH) or protein, e.g., by immunohistochemistry (IHC) targets in each of the multiple specimens in the array. Each microarray block can be sectioned up to 200–300 times. Therefore, tens of thousands of tissue microarray sections can be obtained from a set of tissue specimens in one recipient block. This substantially facilitates molecular profiling of very large numbers of cancer tissues and allows the generation of large-scale correlative databases including clinical information and molecular data (including images), while ensuring that the donor blocks from which the tissue cores are removed can continue to be utilized so that research materials are not destroyed.

In early 1998, Kononen et al. (1) described a tissue microarray "chip" that had been developed for high-throughput molecular profiling of tumor specimens. Tissue microarrays enable rapid in-situ analysis of up to 1000 tumors or other tissues in a single experiment. In the method of Kononen, original tissue sample sources are morphologically representative regions of regular formalin-fixed paraffin-embedded tumor blocks. Core tissue biopsies are taken from individual "donor" paraffin-embedded tumor blocks and precisely arrayed into a new "recipient" paraffin block using a custom built instrument. Thereafter, Bubendorf et al. published data of a survey of gene amplifications during prostate cancer progression by high-throughput fluorescence in-situ hybridization on tissue microarrays (2). The first hand-held paraffin tissue array apparatus was later marketed.

Tissue microarrays consisting of 0.6 mm biopsies of paraffin-embedded tissues have been used for various clinicopathological studies. This size is sufficient for assessing morphological features of the analyzed tissues on many samples. However, the size of the biopsy used in these arrays may not be representative of the whole tumor specimen because of tissue heterogeneity. Additionally, paraffin tissue arrays have distinct limitations in maintaining intact RNA transcription levels, as well as proteins and other molecules (i.e., lipids) due to the fixatives and chemical reagents required for the paraffin process. Thus, tissue microarray technology using paraffin-embedded tissues can reach its limits for the detection of RNA targets or certain proteins. The use of a cryoarray strategy would overcome these limitations and would allow for the processing of multiple frozen tissue specimens and/or cell lines on a single tissue block.

Therefore, it would be beneficial to have an effective means and a system for creating tissue arrays that allow all molecules to be assayed at the expression level and simultaneously visualized at micro-anatomical levels. Specifically, the prior art is deficient in the lack of an effective means/system for creating a cryoarrays for frozen tissue assays. The present invention fulfills this long-standing need and desire in the art.

SUMMARY OF THE INVENTION

In one embodiment of the present invention, there is provided a cryoarray device comprising a mold plate having an upper and a lower surface; mold alignment pins where the mold alignment pins are perpendicularly attached to the lower surface of the mold plate; an ejector plate having an upper surface and a lower surface where the plate has holes between the upper surface and the lower surface; ejector pins having ejector thumb pads attached to an upper surface of the ejectors pins and connecting the mold plate and the ejector plate; and cryoarray pins, of equal number to the holes in the ejector plate and aligned with the holes in the ejector plate.

In another embodiment of the present invention, there is provided a cryoarray system for forming an array for frozen tissue, comprising a tissue mold; an embedding medium filling the tissue mold, frozen within the tissue mold where the frozen embedding medium forms a recipient tissue block; and the cryoarray device which is placed in the tissue mold containing the embedding medium, but prior to freezing the embedding medium; where freezing the embedding medium around the cryoarray pins of the device creates grid holes into the recipient block when the cryoarray device is separated from the recipient block so that an array is formed in the recipient block for frozen tissue.

In yet another embodiment of the present invention, there is provided a method for preparing tissue for assays, comprising the steps of selecting at least one frozen tissue core from a donor block; inserting each of the frozen cores into a grid hole of the recipient block of the cryoarray system disclosed supra thereby forming a frozen tissue array; cutting sections from the array; and assaying the sections.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
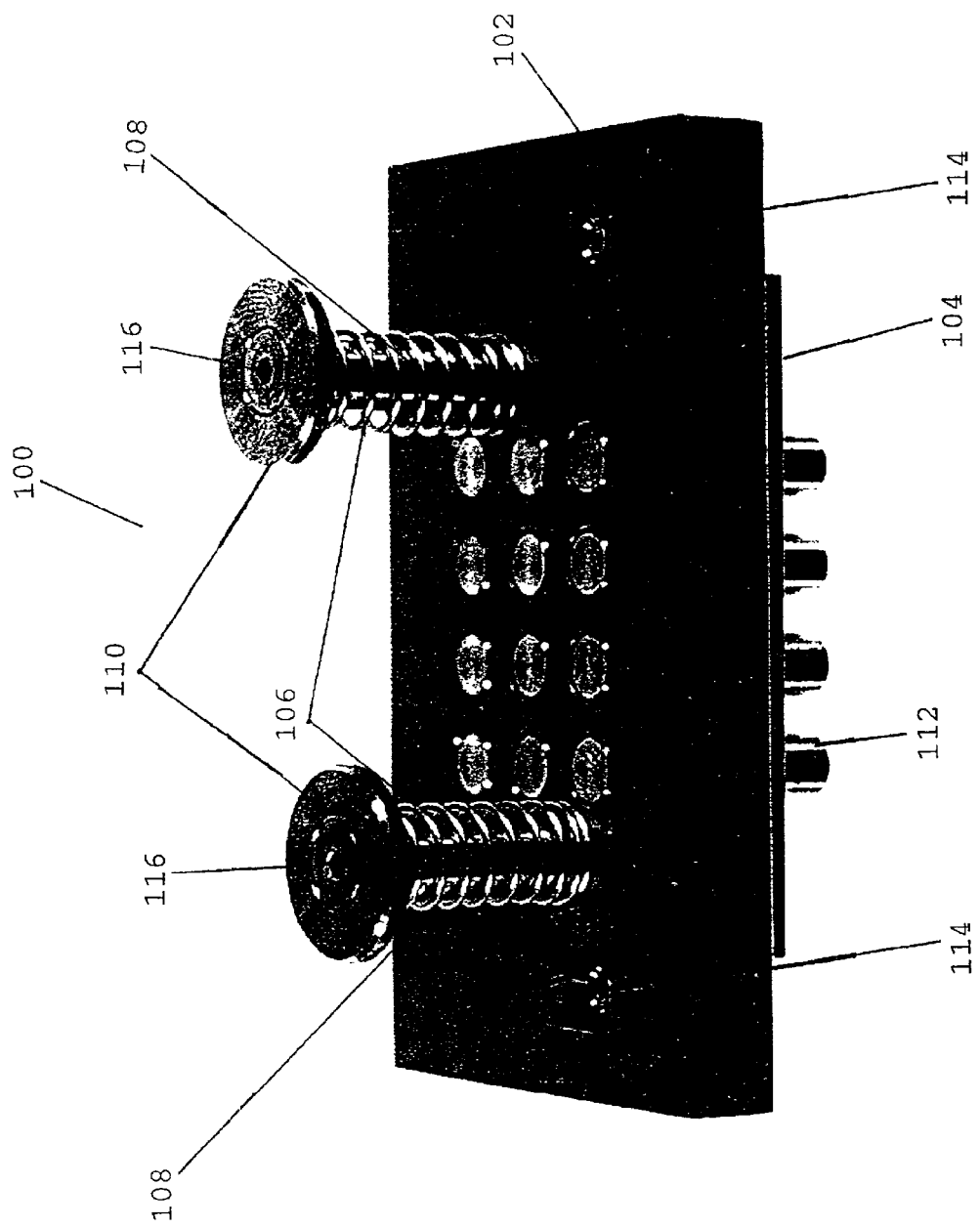
FIG. 1 shows an over view of the cryoarray apparatus 100, comprising a mold plate 102, an ejector plate 104, two ejector/guide springs 106, two ejector/guide pins 108, two ejector thumb pads 110, twelve cryoarray pins 112, two mold alignment pins 114, and two ejector screws 116.

In one embodiment of the present invention, there is provided a cryoarray device comprising a mold plate having an upper and a lower surface; mold alignment pins where the mold alignment pins are perpendicularly attached to the lower surface of the mold plate; an ejector plate having an upper surface and a lower surface where the plate has holes between the upper surface and the lower surface; ejector pins having ejector thumb pads attached to an upper surface of the ejectors pins and connecting the mold plate and the ejector plate; and cryoarray pins, of equal number to the holes in the ejector plate and aligned with the holes in the ejector plate.

In an aspect of this embodiment the mold alignment pins direct the placement of the cryoarray device into a tissue mold. Additionally, the cryoarray pins connect operably to the lower surface of the mold plate and are capable of passing through the holes in said ejector plate. In this aspect the ejector pins are capable of lowering and of raising the ejector plate over the cryoarray pins. Optionally, the cryoarray device may have ejector springs that surround an outer surface of the ejector pins and operably located between the upper surface of the mold plate and the lower surface of one of the ejector thumb pads.

In another embodiment of the present invention, there is provided a cryoarray system for forming an array for frozen tissue, comprising a tissue mold; an embedding medium filling the tissue mold, frozen within the tissue mold where the frozen embedding medium forms a recipient tissue block; and the cryoarray device is placed in the tissue mold containing the embedding medium, but prior to freezing the embedding medium; where freezing the embedding medium around the cryoarray pins of the device creates grid holes into the recipient block when the cryoarray device is separated from the recipient block so that an array is formed in the recipient block for frozen tissue.

In this embodiment of the present invention the recipient block is separated from the cryoarray device by depressing the ejector pins to lower the ejector plate over the cryoarray pins. A representative example of the embedding medium is O.C.T.™ compound. The embedding medium is frozen at temperature of about −20° C. to about −80° C.

In yet another embodiment of the present invention, there is provided a method for preparing tissue for assays, comprising the steps of selecting at least one frozen tissue core from a donor block; inserting each of the frozen cores into a grid hole of the recipient block of the cryoarray system disclosed supra thereby forming a frozen tissue array; cutting sections from the array; and assaying the sections. Representative diameters for the frozen tissue core samples to be assayed are about 1.0 mm to about 3.0 mm in diameter, preferably about 2.5 mm to about 3.0 mm in diameter. Examples of tissue assays that can be performed on the tissue array are morphologic evaluation, in situ hybridization, immunohistochemistry, in situ polymerase chain reaction and fluorescence in situ hybridization.

Provided herein is cryoarray device/system for forming frozen tissue arrays for subsequent analysis. When comparing the instant cryoarray to a paraffin-embedded array, even if the number of specimens that can be analyzed per array is lower than that with paraffin tissue arrays, the cryoarray system provides a significant advantage. Because a core diameter of 3 mm is used in the instant cryoarrays, it may not be necessary to array more than one or two biopsies per specimen, thus increasing the efficiency in comparison with paraffin tissue arrays. Additional advantages of the instant cryoarrays include the use of multiple fixatives to optimize immunohistochemistry (IHC) or in-situ hybridization (ISH) for target probe or antibody assays and the use of the very same samples on which immunohistochemistry or in-situ hybridization is carried out to extract RNA to make cDNA for gene microchip analysis. Embodiments of the present invention are better illustrated with reference to the Figures, however, such reference is not meant to limit the present invention in any fashion.

Figure 2:
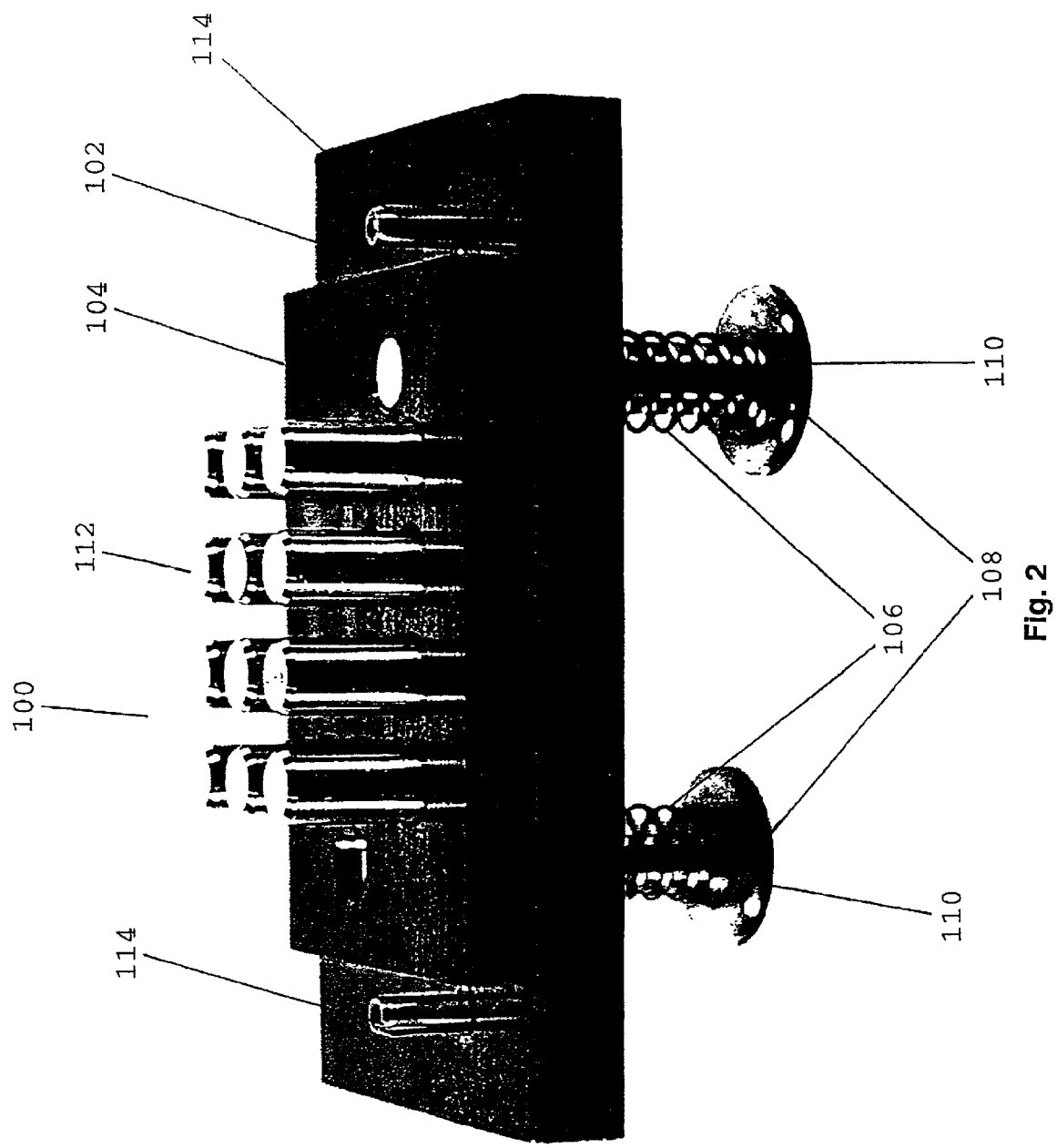
FIG. 2 shows another over view of the cryoarray apparatus 100 from a different angle, which is an upside-down position compared to the view in FIG. 1.
Figure 3:
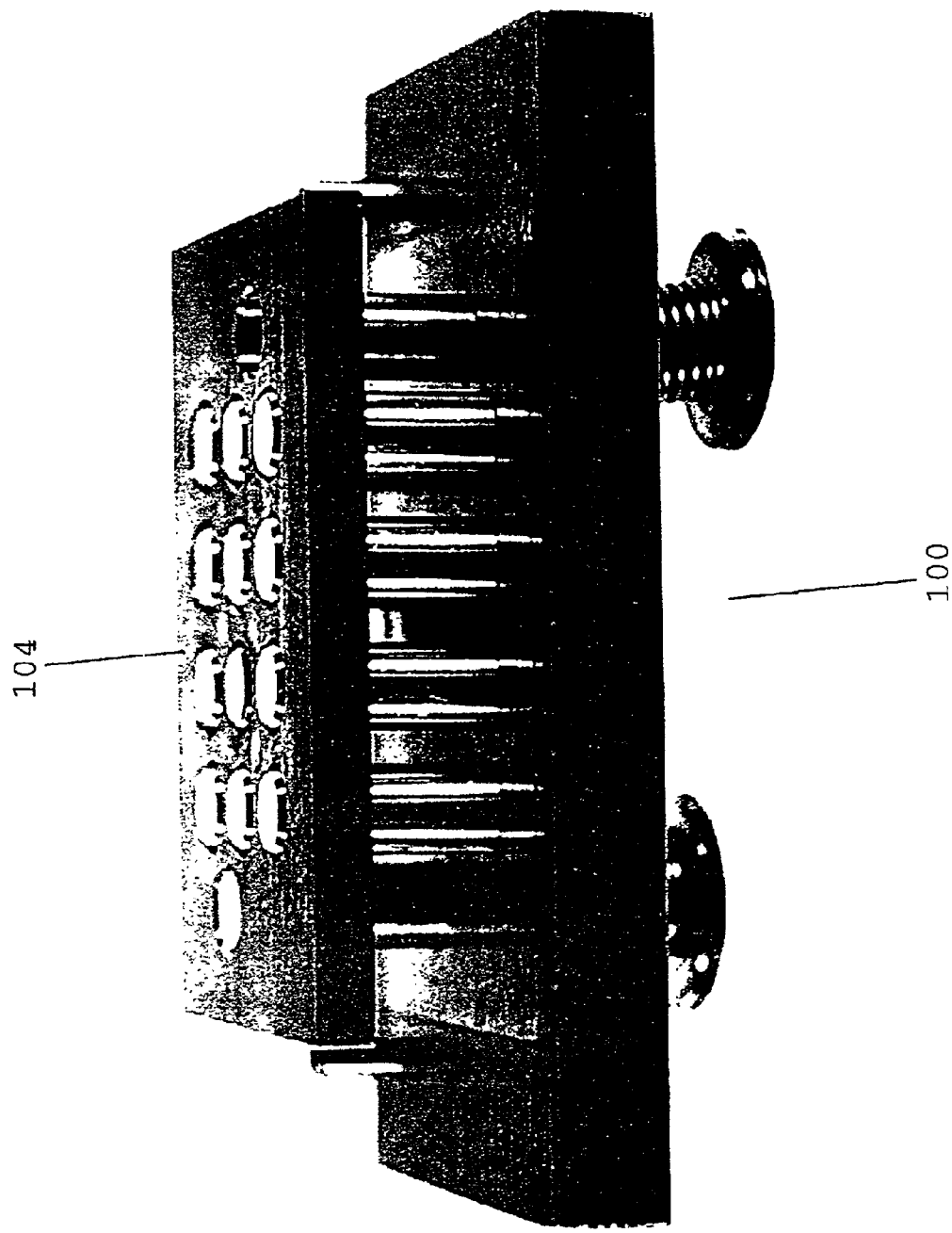
FIG. 3 shows the cryoarray apparatus 100 during the activation of the ejector plate 104.

A representative cryoarray design is shown in FIGS. 1–3. The cryoarray apparatus 100 comprises a mold plate 102, an ejector plate 104, two ejector/guide springs 106, two ejector/guide pins 108, two ejector thumb pads 110, twelve cryoarray pins 112, two mold alignment pins 114, and two ejector screws 116. Furthermore, although the apparatus 100 depicted herein comprises twelve cryoarray pins 112, the number of pins in the cryoarray need not be limited to twelve, e.g., a forty-eight compartment cryoarray can increase the number of cores in a cryoarray, thereby increasing the size of the assay data set. The diameter of the cryoarray pins 112 is about 3 mm. Table 1 lists each component of the cryoarray as well as the material of which each component is made.

TABLE 1

Components of Cryoarray System 100

| Reference # | Title | Material | Quantity |
| --- | --- | --- | --- |
| 102 | Mold Plate | Brass | 1 |
| 104 | Ejector Plate | Brass | 1 |
| 106 | Ejector/Guide Spring | Stainless Steel | 2 |
| 108 | Ejector/Guide Pin | Stainless Steel | 2 |
| 112 | Cryoarray Pin (variable number) | Stainless Steel | 12 (as shown) |
| 114 | Mold Alignment Pin | Stainless Steel | 2 |
| 110 | Ejector Thumb Pad | Brass | 2 |
| 116 | Ejector Screw | Stainless Steel | 2 |

Figure 4:
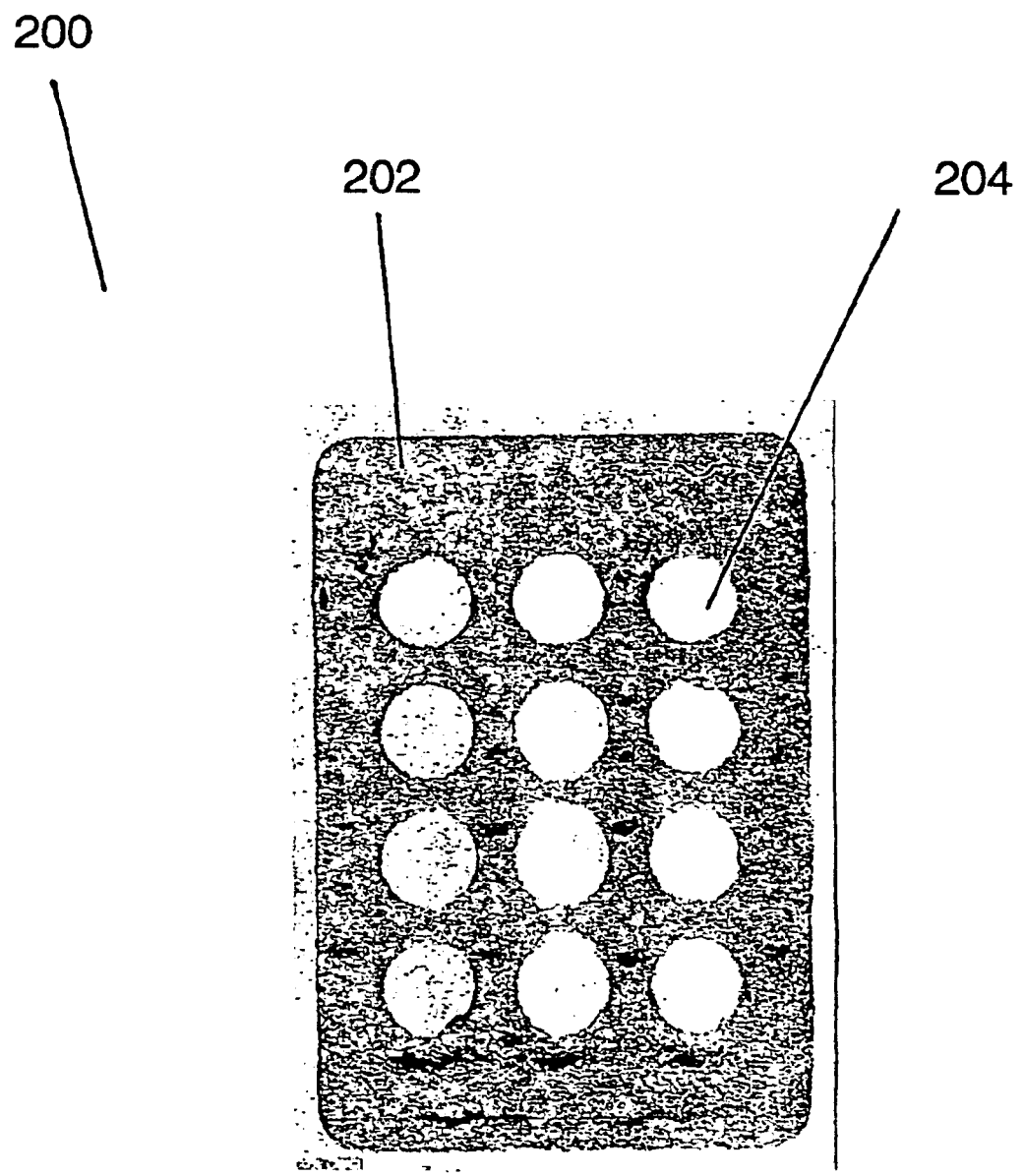
FIG. 4 shows the frame 202 with a twelve hole grid 204 that forms the frozen tissue array 200.

With reference to FIG. 4 and continued reference to FIGS. 1–3, the cryoarray apparatus 100 is used with a tissue mold (not shown) to form a cryoarray or frozen tissue array system comprising a single recipient block 200 of arrayed multiple biopsies taken from embedded frozen tissues. The recipient block 200 is a frame of embedding compound 202 containing multiple preformed holes 204 having a diameter of about 3.0 mm.

As is standard in the art, a plastic mold for frozen tissue is filled with a liquid embedding medium to the fill line indicated on the tissue mold. A representative example of a tissue mold is Cryomold having 37 cm×24 cm dimensions (Simport, Montreal, Canada) and of an embedding medium is optimal cutting temperature compound or O.C.T.™ compound (SAKURA FINETEK, Torrance, Calif.). O.C.T.™ compound has a freezing point of 0° C.

The cryoarray apparatus 100 is placed into the Cryomold (not shown) as directed by the mold alignment pins 114. The cryoarray pins 112 displace the liquid embedding compound and create a grid of holes 204 framed by the embedding compound 202. The tissue mold containing the cryoarray 100 is then placed at about −20° C. to about −80° C. for about 15 minutes or until the liquid embedding compound is solidified and thus forms the recipient block in the cryoarray 200.

Once the embedding compound is frozen, the ejector pins 108 on the cryoarray device 100 are depressed, activating the ejector plate 104 which lowers over the cryoarray pins 112. This releases the frozen recipient block in the cryoarray 200 which comprises the frozen embedding compound frame 202 having a grid of holes 204 equal to the number of cryoarray pins 112 that form the cryoarray or frozen tissue array 200.

Figure 5:
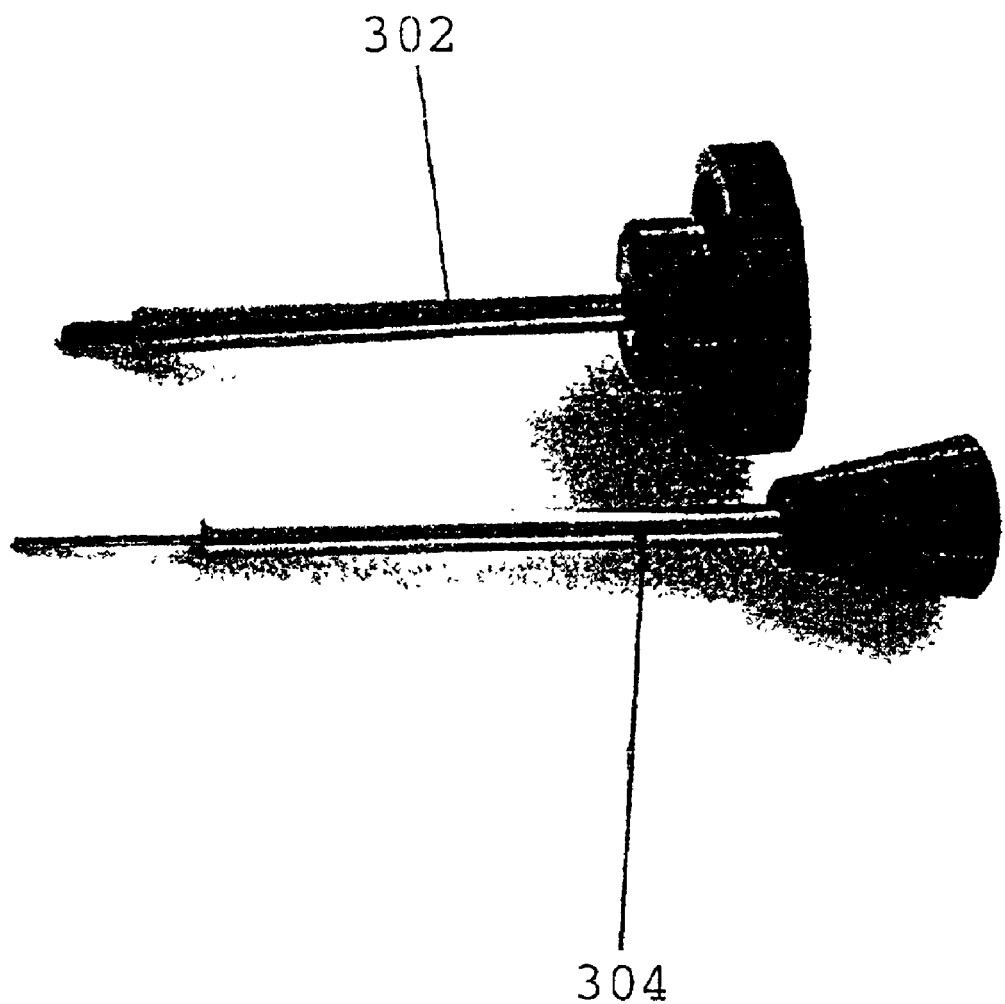
FIG. 5 shows a biopsy needle 302 of 3 mm diameter (top) and a piston 304 insertable into the core of the biopsy needle.
Figure 6:
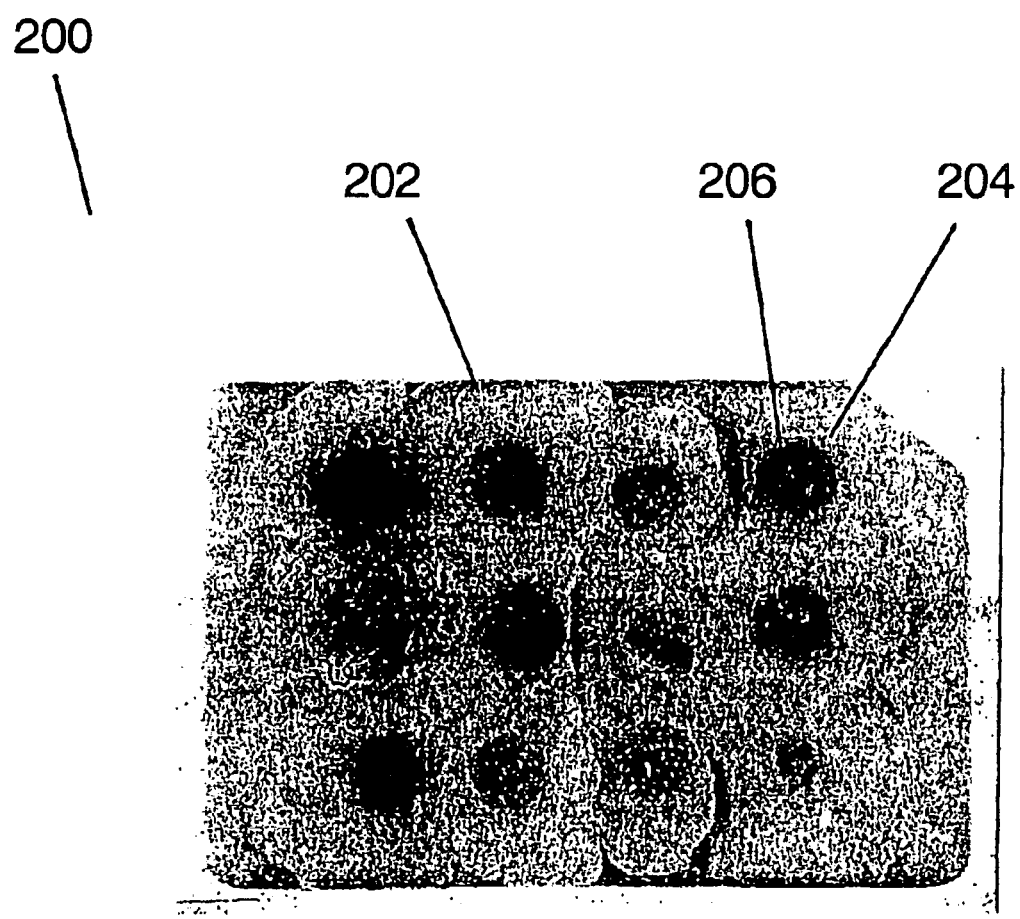
FIG. 6 shows the final form of the frozen tissue array 200 including frozen cores 206 taken from normal tissue donor blocks.

With reference to FIGS. 5 and 6 and continued reference to FIG. 4, a specifically designed core biopsy needle 302 of 3 mm diameter is used to punch core specimens 206 from identified areas of frozen donor tissue blocks (not shown). The strong core needle 302 punches a hole in the identified area of the donor block and the piston 304 is inserted into the core needle 302 in order to release the punched frozen specimen core 206 into one of the grid holes 204 of the recipient block in the cryoarray 200 in a manner similar to and standard for paraffin-embedded tissues and known to one of ordinary skill in the art. The core samples 206 preferably have a diameter of about 2.5 mm to 3.0 mm. It is to be understood that when using the cryoarray 200, frozen cores of less than 1 mm in diameter usually become friable and can break apart. Thus, a particularly fine needle diameter may be optimal for removing a frozen core from donor blocks.

Figure 7:
FIG. 7 shows a hematoxylin and eosin stained section used for morphological evaluation of the above normal tissue array.

The further processing of the cryoarray 200 follows the general guidelines for embedded frozen tissue samples, particularly for samples embedded in O.C.T.™. Frozen sections are generated using a tape-based sectioning system (Instrumedics, Hackensack, N.J.). Sections cut from the cryoarray 200 allow parallel detection of DNA (e.g. by fluorescence in-situ hybridization), RNA (e.g. by mRNA ISH) or protein (e.g. by immunohistochemical analysis) targets in each of the specimens 206 in the cryoarray 200. FIG. 7 depicts a hematoxylin and eosin stained section of the frozen tissue specimen 206.

Cell proliferation, differentiation, death and genomic integrity is controlled by a multitude of genes and signaling pathways in cancer development. Through new techniques, such as cDNA microarrays, the expression of thousands of genes can be measured in a single experiment. As such, analysis of thousands of specimens from patients at different stages of disease can be comprehensively surveyed. The potential uses of the cryoarray disclosed herein include analyzing molecular basis of tumor progression; obtaining molecular profiling of thousands of tumors with hundreds of biomarkers; validation of cDNA microarray screening data; rapid translation of results from cell line and animal models to human cancer; evaluation of the diagnostic, prognostic and therapeutic potential of newly discovered genes and molecules; testing and optimization of probes and antibodies; improved utilization of pathology archives and tissue banks; and international, large scale collaborations for multi-center molecular profiling of tumors.

The following references were cited herein.

1. Kononen et al., 1998, Nature Medicine 4: 844–847.
2. Bubendorf et al., 1999, Cancer Research 59: 803–806.

Any patents or publications mentioned in this specification are indicative of the levels of those skilled in the art to which the invention pertains. These patents and publications are herein incorporated by reference to the same extent as if each individual publication was indicated specifically and individually to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A cryoarray device comprising:
    a mold plate having an upper and a lower surface;
    mold alignment pins, said mold alignment pins perpendicularly and positionally attached to the lower surface of said mold plate to direct placement of said device into a tissue mold;
    an ejector plate having an upper surface and a lower surface, said plate comprising holes between said upper surface and said lower surface;
    ejector pins, said ejector pins comprising ejector thumb pads attached to an upper surface of said pins, said ejector pins operably attached to said ejector plate and connect said ejector plate and said mold plate;
    ejector springs, each of said springs surrounding an outer surface of each of said ejector pins and operably located between said upper surface of said mold plate and said lower surface of one of said ejector thumb pads; and
    cryoarray pins, said cryoarray pins equal in number to said holes in said ejector plate and aligned with said holes in said ejector plate.

2. The cryoarray device of claim 1, wherein said cryoarray pins are attached operably to the lower surface of said mold plate to pass through said holes in said ejector plate.

3. The cryoarray device of claim 1, wherein said ejector pins are attached to said ejector plate through said mold plate to lower and to raise said ejector plate.

4. A cryoarray system for forming an array for frozen tissue, comprising:
    a tissue mold;
    an embedding medium, said embedding medium filling said tissue mold, said embedding medium capable of being frozen therein, said frozen embedding medium forming a recipient tissue block, and
    the cryoarray device of claim 1, said device placed in said tissue mold with said embedding medium, but prior to freezing said embedding medium;
    wherein freezing said embedding medium around said cryoarray pins of the device of claim 1 creates grid holes into said recipient block upon separation of said cryoarray device from said recipient block thereby forming an array in said recipient block for frozen tissue.

5. The cryoarray system of claim 4, wherein said embedding medium is O.C.T.™ compound.

6. The cryoarray system of claim 4, wherein said embedding material is frozen at a temperature of about −20° C. to about −80° C.

7. The cryoarray system of claim 4, wherein said recipient block is separated from said cryoarray device by depressing said ejector pins to lower said ejector plate over said cryoarray pins.

8. A method for preparing tissue for assays, comprising the steps of:

selecting at least one frozen tissue core from a donor block;

inserting each of said at least one frozen core into said grid holes of said recipient block of the cryoarray system of claim;

cutting sections from said array; and assaying said sections.

9. The method of claim 8, wherein said tissue is from about 1.0 mm to about 3.0 mm in diameter.

10. The method of claim 9, wherein said tissue is from about 2.5 mm to about 3.0 mm in diameter.

11. The method of claim 8, wherein said tissue assay is selected from the group consisting of morphologic evaluation, in situ hybridization, immunohistochemistry, in situ polymerase chain reaction and fluorescence in situ hybridization.

* * * * *